United States Patent
Manoux et al.

(10) Patent No.: US 8,985,427 B1
(45) Date of Patent: Mar. 24, 2015

(54) FEEDER BELT WITH INTERNALLY MANUFACTURED STAPLES FOR TRUE MULTI-FIRE SURGICAL STAPLER

(75) Inventors: Philipe R. Manoux, San Francisco, CA (US); Bryan D. Knodel, Flagstaff, AZ (US); Patrick Flanagan, San Diego, CA (US)

(73) Assignee: Cardica, Inc., Redwood City, CA (US)

( * ) Notice: Subject to any disclaimer, the term of this patent is extended or adjusted under 35 U.S.C. 154(b) by 1291 days.

(21) Appl. No.: 12/435,912

(22) Filed: May 5, 2009

(51) Int. Cl.
*A61B 17/068* (2006.01)

(52) U.S. Cl.
CPC ............................... *A61B 17/068* (2013.01)
USPC ..................... 227/175.1; 227/19; 606/219

(58) Field of Classification Search
USPC ............ 227/157.1, 176.1, 51, 61–62, 83, 95, 227/901, 902; 411/920; 606/219
See application file for complete search history.

(56) References Cited

U.S. PATENT DOCUMENTS

| | | | | |
|---|---|---|---|---|
| 2,964,751 | A | * | 12/1960 | Lang ............................. 29/432.1 |
| 3,170,279 | A | * | 2/1965 | Dubini ............................... 59/77 |
| 3,581,551 | A | | 6/1971 | Wilkinson |
| 3,650,453 | A | | 3/1972 | Smith, Jr. |
| 3,899,914 | A | | 8/1975 | Akiyama |
| 4,043,504 | A | * | 8/1977 | Hueil et al. .................... 227/116 |
| 4,086,926 | A | | 5/1978 | Green et al. |
| 4,206,863 | A | * | 6/1980 | Savino ............................. 227/83 |
| 4,228,895 | A | | 10/1980 | Larkin |
| 4,328,918 | A | * | 5/1982 | Yoshida ........................... 227/83 |
| 4,475,679 | A | | 10/1984 | Fleury, Jr. |
| 4,583,276 | A | * | 4/1986 | Olesen .......................... 29/432.1 |
| 4,619,391 | A | * | 10/1986 | Sharkany et al. ................ 227/19 |
| 4,633,861 | A | | 1/1987 | Chow et al. |
| 4,669,647 | A | * | 6/1987 | Storace ............................ 227/19 |
| 4,762,260 | A | | 8/1988 | Richards et al. |
| 4,969,591 | A | | 11/1990 | Richards et al. |
| 5,156,315 | A | | 10/1992 | Green et al. |
| 5,192,288 | A | * | 3/1993 | Thompson et al. ........... 606/143 |
| 5,413,272 | A | | 5/1995 | Green et al. |
| 5,476,206 | A | | 12/1995 | Green |
| 5,655,698 | A | | 8/1997 | Yoon |
| 5,662,260 | A | | 9/1997 | Yoon |
| 5,692,668 | A | | 12/1997 | Schulze et al. |

(Continued)

FOREIGN PATENT DOCUMENTS

| | | |
|---|---|---|
| EP | 1238634 | 9/1994 |
| JP | 2005160933 | 6/2005 |

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Andrew M Tecco
(74) *Attorney, Agent, or Firm* — Cardica, Inc.

(57) ABSTRACT

An exemplary surgical apparatus may include a feeder belt; wings fixed to that feeder belt; and a die into which the feeder belt extends, where relative motion of the die and feeder belt bends at least one wing to transform at least one wing into an unformed staple. An exemplary surgical method for treating tissue of a patient may include providing a surgical instrument including an end effector; placing the end effector adjacent to tissue of a patient; and manufacturing at least one surgical staple within the end effector.

9 Claims, 7 Drawing Sheets

(56) References Cited

U.S. PATENT DOCUMENTS

| | | | |
|---|---|---|---|
| 5,810,855 A | 9/1998 | Rayburn et al. | |
| 5,816,471 A | 10/1998 | Plyley et al. | |
| 5,855,311 A | 1/1999 | Hamblin et al. | |
| 5,894,979 A | 4/1999 | Powell | |
| 5,908,149 A * | 6/1999 | Welch et al. | 227/176.1 |
| 5,918,791 A | 7/1999 | Sorrentino et al. | |
| 5,964,774 A | 10/1999 | McKean et al. | |
| 6,086,304 A * | 7/2000 | Hujishima et al. | 411/443 |
| 6,306,149 B1 | 10/2001 | Meade | |
| 6,391,038 B2 | 5/2002 | Vargas et al. | |
| 6,602,252 B2 | 8/2003 | Mollenauer | |
| 6,716,232 B1 | 4/2004 | Vidal et al. | |
| 6,817,508 B1 | 11/2004 | Racenet | |
| 6,843,403 B2 | 1/2005 | Whitman | |
| 7,025,747 B2 | 4/2006 | Smith | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,510,106 B2 * | 3/2009 | Manabe | 227/107 |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 * | 5/2007 | Boudreaux et al. | 606/157 |
| 2007/0125828 A1 | 6/2007 | Rethy et al. | |
| 2008/0078807 A1 | 4/2008 | Hess et al. | |

FOREIGN PATENT DOCUMENTS

| | | |
|---|---|---|
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparoscopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology 18*(9), (Nov. 2004),811-817.

Steichen, Felicien M., et al., "Mechanical Sutures in Surgery", *Brit. J. Surg. 60*(3), (Mar. 1973),191-197.

"Cardica Microcutter Implant Delivery Device 510(k), Cover Sheet, Table 10.1, "Substantial Equivalence Comparison," and Section 12, "Substantial Equivalence Discussion"".

* cited by examiner

FEEDER BELT WITH INTERNALLY MANUFACTURED STAPLES FOR TRUE MULTI-FIRE SURGICAL STAPLER

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to locate the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use disposable cartridges. That endocutter is described in, for example, U.S. patent application Ser. No. 12/263,171, filed on Oct. 31, 2008 (the "Endocutter Document"), which is hereby incorporated by reference in its entirety. In order to accomplish such multiple firing, a feeder belt is used, to which a plurality of staples are attached. The staples are sheared from the feeder belt during firing of the endocutter. The feeder belt is long and thin. The feeder belt can extend through a shaft of the tool and into a stapler head that engages tissue.

BRIEF DESCRIPTION OF THE DRAWINGS

The use of the same reference symbols in different figures indicates similar or identical items.

DETAILED DESCRIPTION

The Endocutter Document describes exemplary feeder belts used in a surgical stapler. In certain surgical applications, it may be advantageous to reduce the profile of the end effector of the surgical stapler. Further, where the surgical stapler is articulated, it may be simpler to advance the feeder belt to the end effector where the staples have not yet been created.

Referring to FIGS. 1-4, at least one feeder belt 2 may extend into an die 4 in the end effector of the surgical stapler. Alternately, the die 4 may be located in a different position within the surgical stapler. A plurality of wings 6 may extend from the feeder belt 2 proximal to the die 4. The feeder belt 2 may be substantially planar, and the wings 6 may be in substantially the same plane as the feeder belt 2. In this way, the feeder belt 2 and wings 6 collectively are in the same plane, minimizing the thickness of any passage or aperture in the surgical stapler through which they collectively pass. Each wing 6 may include a free end 10 and a second, opposite end 12 fixed to the feeder belt 2.

The die 4 includes at least one contact surface 8. The contact surface 8 may be angled downward and outward, at least in part, and the angle of the contact surface 8 relative to the plane of the feeder belt 2 increases from the proximal to the distal direction. The wings 6 may be arranged on both lateral sides of the feeder belt 2, such that the wings 6 are arranged in two rows on opposite sides of the feeder belt 2. Alternately, the wings 6 are arranged differently on the feeder belt 2, or into one row or three or more rows. Advantageously, the die 4 provides a different contact surface 8 corresponding to each row of wings 6. Alternately, the contact surface 8 is not angled, but rather is curved at least in part.

The die 4 may be held in a substantially fixed position relative to the feeder belt 2, such as within the end effector of the surgical stapler. The feeder belt 2 may be advanced distally relative to the die 4, where that advancement may be performed such as set forth in the Endocutter Document. As the feeder belt 2 is moved distally, one or more wings 6 enter the die 4 and encounter an contact surface 8. For simplicity, such contact is described with respect to a single wing 6. As the feeder belt 2 advances distally, a wing 6 encounters the proximal end of a corresponding contact surface 8. The contact surface 8, at its proximal end, is angled or curved slightly out of plane relative to the wing 6, in such a manner that contact between the wing 6 and the contact surface 8 exerts a force on the wing 6 that bends the wing 6 slightly downward relative to the feeder belt 2 and relative to its previous position. As the wing 6 moves distally through the die, the contact surface 8 angles or curves to a progressively greater degree, such that the wing 6 continues to bend downward relative to the feeder belt 2 and the original orientation of the wing 6. Advantageously, the wing 6 bends at or in proximity to the end 12 of the wing 6 fixed to the feeder belt 2, and the wing 6 itself remains in substantially a single plane, where than plane angles away from the plane of the feeder belt 2 an increasing amount as the wing 6 moves distally. At the distal end of the contact surface 8, the angled or curved surface is angled substantially ninety degrees relative to the feeder belt 2, such that the wing 6 is oriented at substantially a ninety degree angle relative to the feeder belt 2. Alternately, the final angle of the wing 6 relative to the feeder belt 2 may be different than substantially ninety degrees. The wing 6 has been bent to a second angle relative to the feeder belt 2 that is different from the first angle that the wing 6 made with the feeder belt 2. At this point, the wing 6 has been transformed into a staple 14, and the staple 14 is pulled out of the distal end of the die 4 by the distal motion of the feeder belt 2. The staples 14 exiting the feeder belt 2 are unformed, and may be configured substantially as set forth in the Endocutter Document. The unformed staples 14 are configured for deployment into tissue, as set forth in the Endocutter Document. Each staple 14 is frangibly connected to the feeder belt 2 upon its exit from the die. Optionally, such frangibility may result from stress exerted on the end 12 of the staple 14 connected to the feeder belt 2. That is, the wings 6 optionally may be connected to the feeder belt 2 strongly enough that they are not frangibly connected to the feeder belt 2, and such that the weakening of the end 12 of the wing 6 connected to the feeder belt 2 by rotation of the wing 6 relative to the feeder belt 2 renders the unformed staple 14 frangible from the feeder belt 2.

Figure 1:
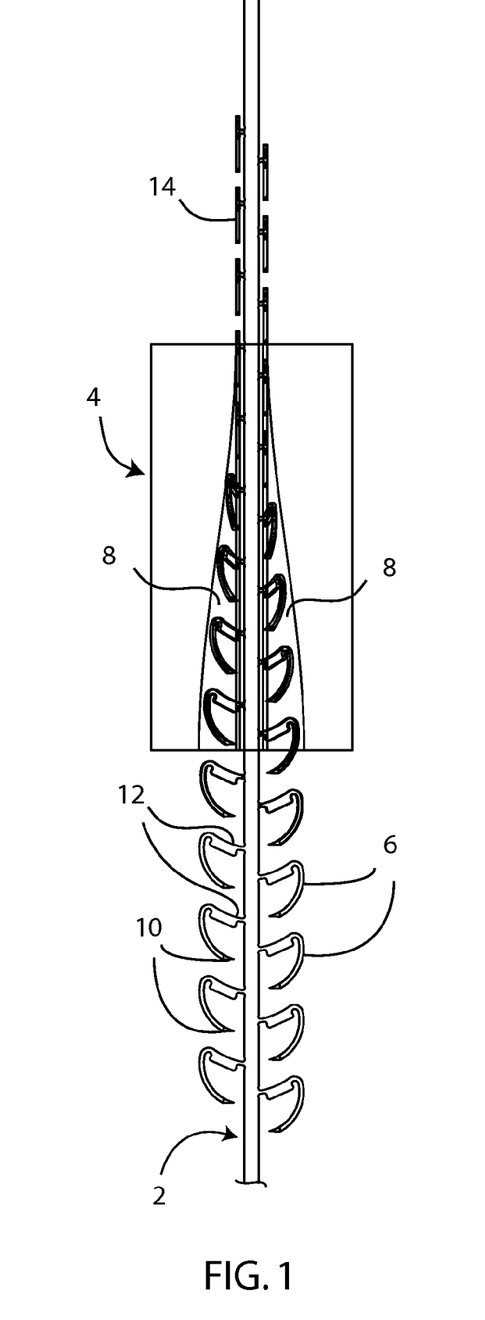
FIG. 1 is a bottom cutaway view of an exemplary feeder belt within a first exemplary die.
Figure 2:
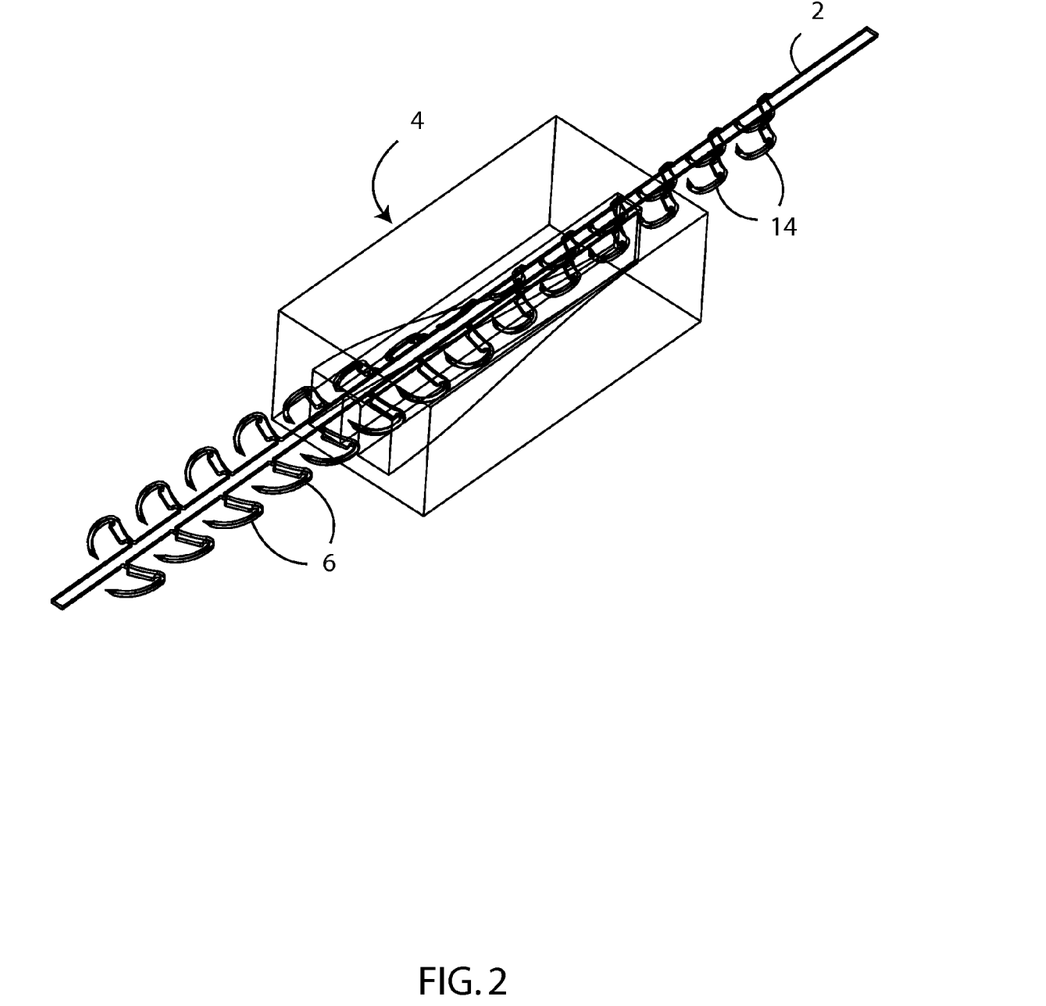
FIG. 2 is a perspective view of the feeder belt and die of FIG. 1, with the die in phantom view.
Figure 3:
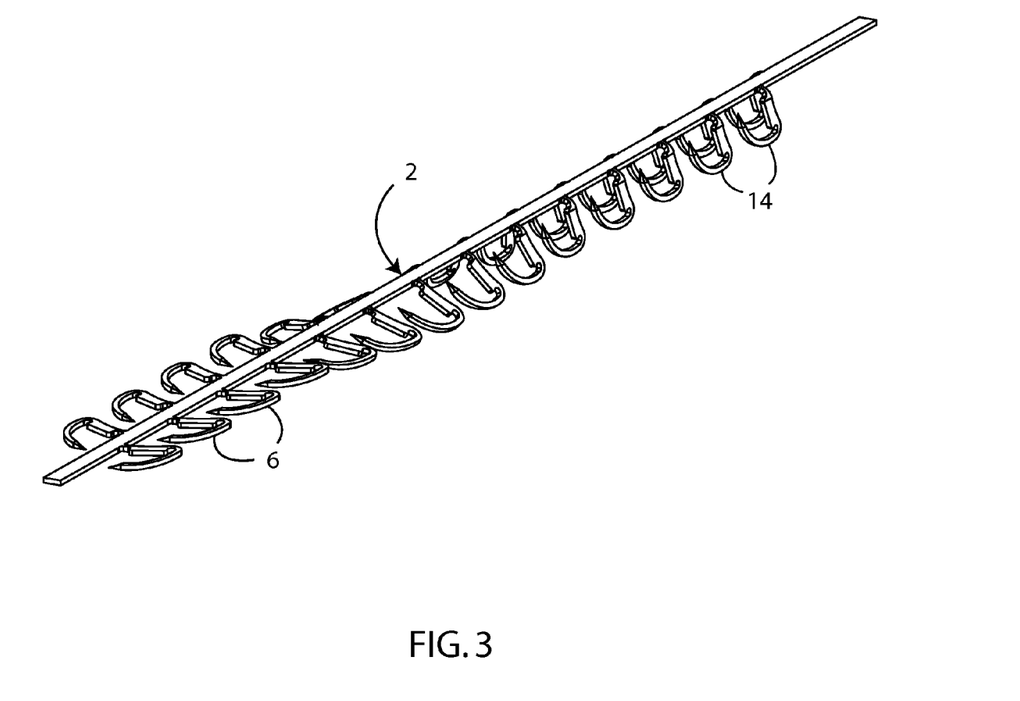
FIG. 3 is a perspective view of the feeder belt of FIG. 1, with the die removed for clarity.
Figure 4:
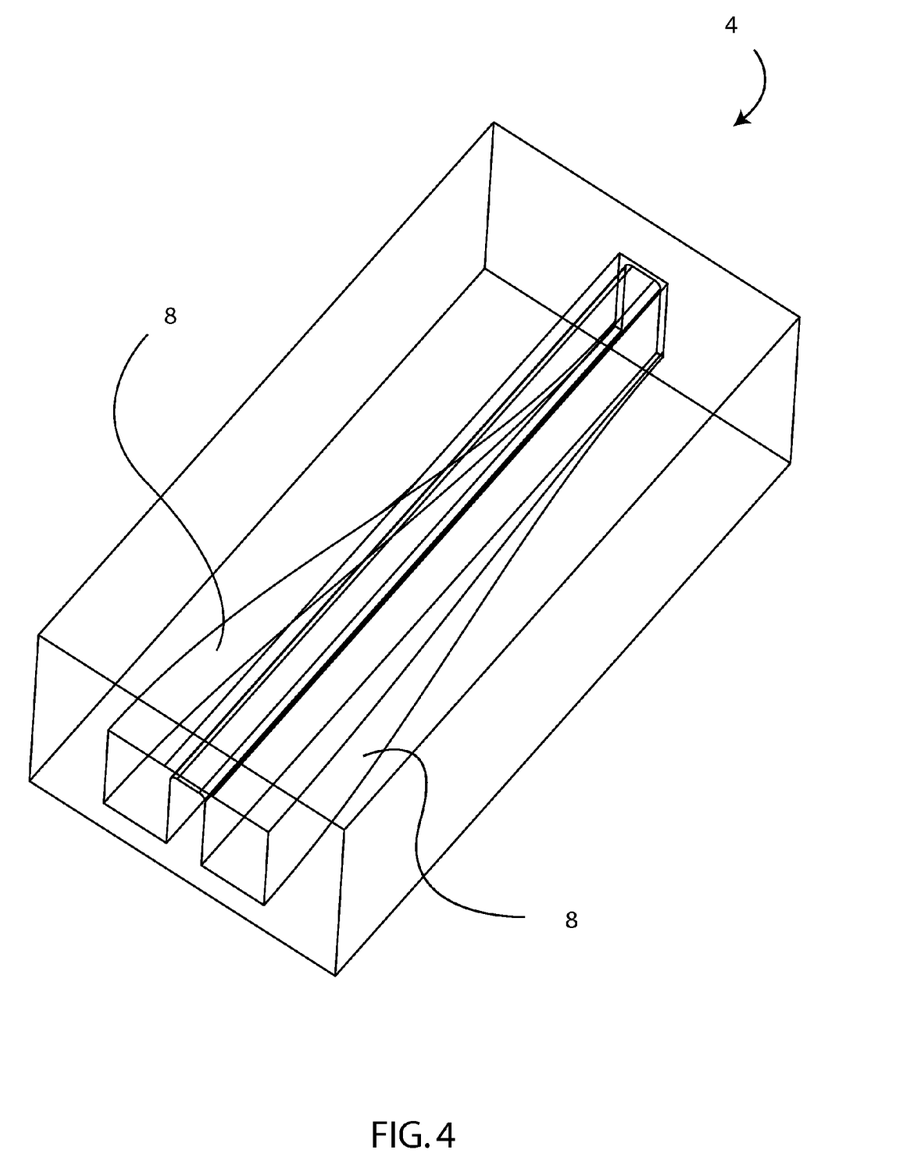
FIG. 4 is a perspective phantom view of the die of FIG. 1.

As seen most clearly in FIG. 3, staples 14 may be progressively formed from wings 6 with the die 4, such that the angle that each wing 6 of several within the die 4 is different from one or more of the others, until the wing 6 has reached the distal end of the die 4 and been formed into a staple 14.

As a result of motion of the feeder belt 2 through the die 4, staples 14 are manufactured by the die 4. Where the die 4 is located in the end effector of the surgical stapler, the staples 14 are manufactured within the end effector, such that manufacture of the staples 14 may be performed within a patient while the end effector is adjacent to tissue of the patient, or otherwise located within a patient. The wings 6 are not staples, because they are not oriented in a fashion in which they can be deployed into tissue. The wings 6 must be bent and reoriented by the die 4 before they can be deployed into tissue of a patient.

Figure 5:
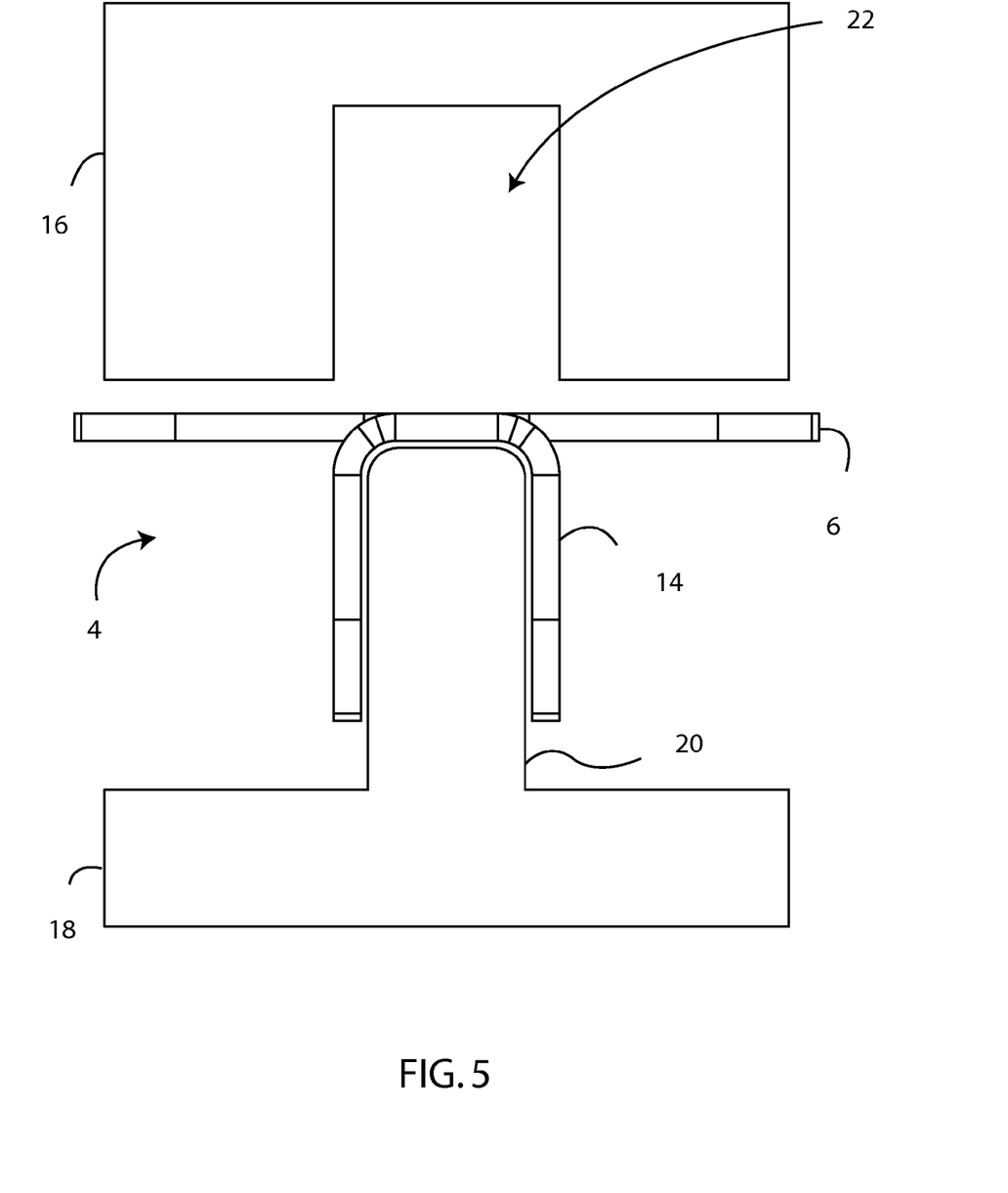
FIG. 5 is an end view of an exemplary feeder belt within a second exemplary die, with the die in an open configuration.
Figure 6:
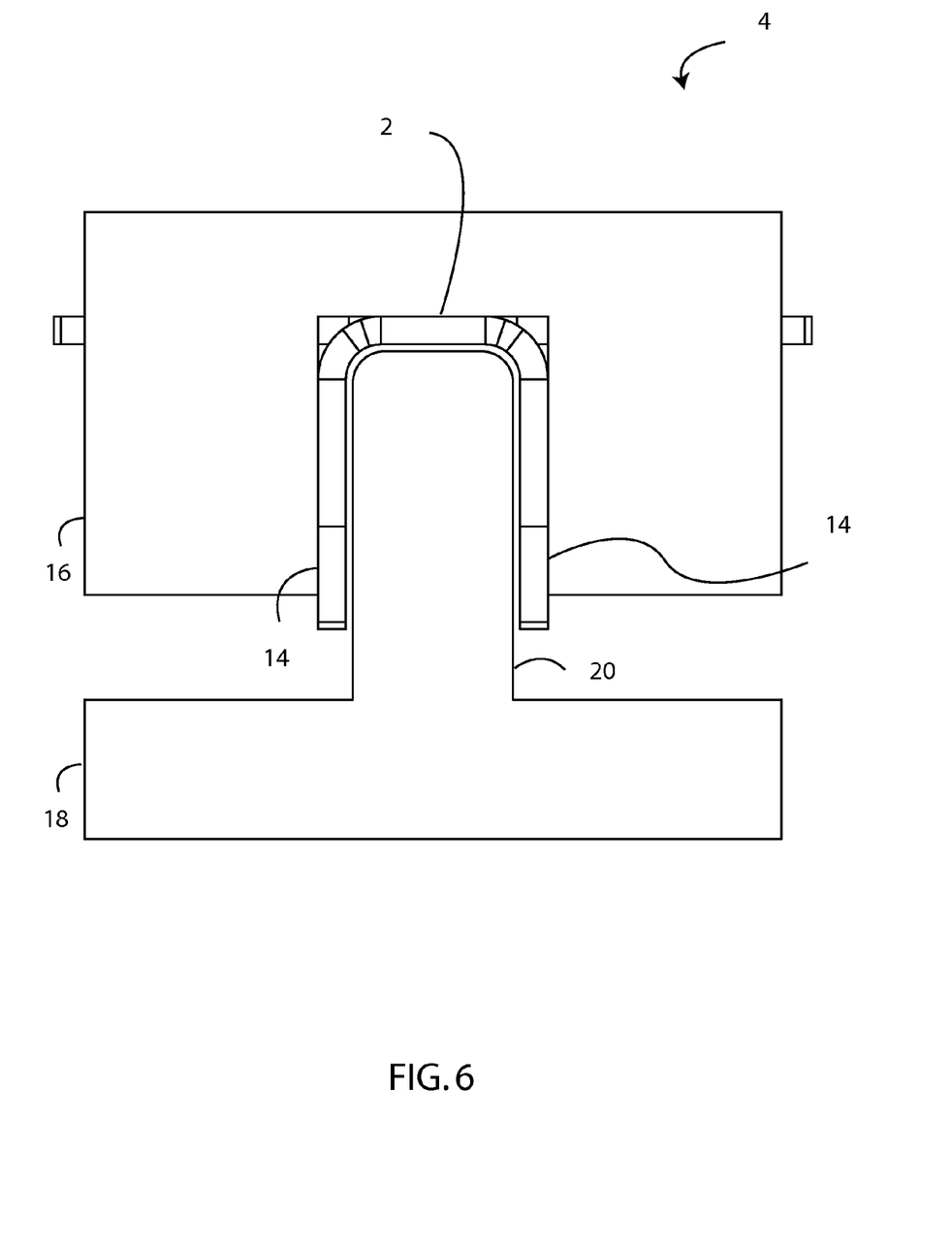
FIG. 6 is an end view of the feeder belt and die of FIG. 5, with the die in a closed configuration.
Figure 7:
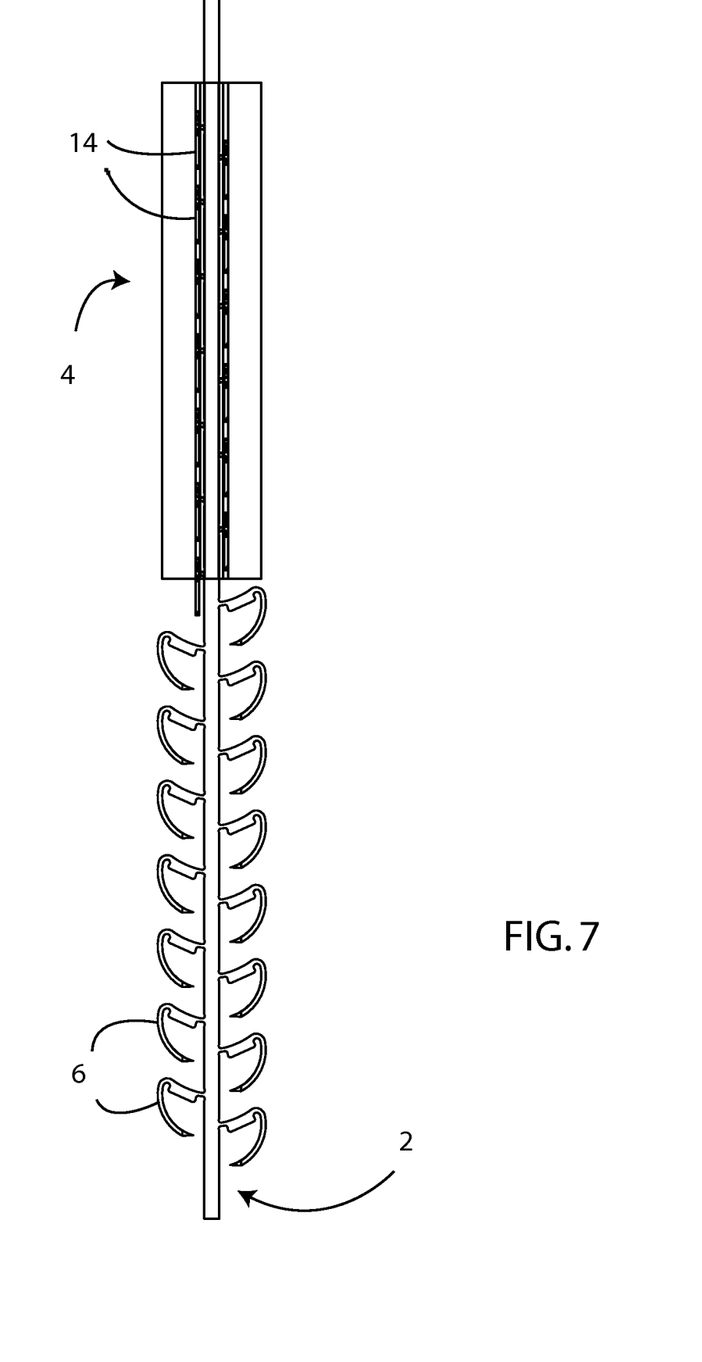
FIG. 7 is a top view of the feeder belt and die of FIG. 5, with the die shown in cutaway.

Referring to FIGS. 5-7, a different die may be utilized to manufacture staples 14 within the surgical instrument. The die 4 may include an upper piece 16 and a lower piece 18. At least one of the upper piece 16 and lower piece 18 is movable relative to the other. The lower piece 18 may include a ridge 20, the upper surface of which supports or otherwise contacts the underside of the feeder belt 2. The upper piece 16 may include a cavity 22 shaped substantially the same as, and slightly larger than, the ridge 20.

Referring also to FIG. 6, the die 4 begins to close as the upper piece 16 and/or lower piece 18 move toward one another, the upper piece 16 bends the wings 6 below it, while the ridge 20 supports the feeder belt 2. The feeder belt 2 may be substantially stationary relative to the die 4 as the die closes. Advantageously, the wing 6 bends at or in proximity to the end 12 of the wing 6 fixed to the feeder belt 2, and the wing 6 itself remains in substantially a single plane, where than plane angles away from the plane of the feeder belt 2 an increasing amount as the die 4 closes. When the die 4 is completely closed, such that the upper piece 16 and/or lower piece 18 no longer move toward one another, the wings 6 within the die 4 may be oriented at substantially a ninety degree angle relative to the feeder belt 2. Alternately, the final angle of the wings 6 relative to the feeder belt 2 may be different than substantially ninety degrees. The wings 6 have been bent to a second angle relative to the feeder belt 2 that is different from the first angle that the wing 6 made with the feeder belt 2. At this point, the wings 6 in the die 4 have been transformed into staples 14, and the staples 14 are pulled out of the distal end of the die 4 by the distal motion of the feeder belt 2. The staples 14 exiting the feeder belt 2 are unformed, and may be configured substantially as set forth in the Endocutter Document.

Optionally, the upper piece 16 and lower piece 20 may be moved to close the die 4 by closing the end effector of the surgical stapler, as set forth in the Endocutter Document. For example, the upper piece 16 may be held in the anvil of the surgical stapler, and the lower piece 20 may be held in the staple holder of the surgical stapler, such that closure of the end effector of the surgical stapler closes the die 4 and transforms the wings 6 within the die 4 into unformed staples 14.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
    a feeder belt;
    a plurality of wings fixed to said feeder belt; and
    a die into which said feeder belt extends, wherein relative motion of said die and said feeder belt bends at least one said wing to transform said at least one wing into an unformed staple;
    wherein at least a portion of said feeder belt is retained within said die after at least one said wing is transformed into at least one said unformed staple.

2. The surgical apparatus of claim 1, wherein said wings are substantially in the same plane as said feeder belt.

3. The surgical apparatus of claim 1, wherein each said wing comprises a first end fixed to said feeder belt and a second, free end.

4. The surgical apparatus of claim 1, wherein each said staple comprises a first end frangibly connected to said feeder belt and a second, free end.

5. The surgical apparatus of claim 1, wherein each said unformed staple is oriented at substantially a right angle to said feeder belt.

6. The surgical apparatus of claim 1, wherein said die includes a contact surface shaped such that distal motion of said feeder belt urges at least one said wing against said contact surface to bend said at least one wing.

7. The surgical apparatus of claim 6, wherein said contact surface is substantially fixed in location.

8. The surgical apparatus of claim 1, wherein said die includes two pieces, at least one of which is movable relative to the other in a direction substantially perpendicular to said feeder belt to close the die, wherein closure of said die bends at least one said wing.

9. The surgical apparatus of claim 8, wherein said die is movable relative to said feeder belt when said feeder belt is substantially stationary.

* * * * *